United States Patent [19]

Petersen

[11] Patent Number: 5,367,901
[45] Date of Patent: Nov. 29, 1994

[54] AIRCRAFT ANALYZER TO DETERMINE MAXIMUM SAFE ALTITUDE FOR A GIVEN BATCH OF FUEL

[76] Inventor: Todd L. Petersen, 984 K Rd., Minden, Nebr. 68959

[21] Appl. No.: 171,397

[22] Filed: Dec. 22, 1993

[51] Int. Cl.$^5$ .................... G01N 7/14; F02M 13/04
[52] U.S. Cl. .................... 73/64.45; 73/53.01; 73/118.1; 137/599; 137/566; 137/567
[58] Field of Search ............... 73/53.01, 64.45, 118.1; 137/599, 566, 567

[56] References Cited

U.S. PATENT DOCUMENTS

| | | | |
|---|---|---|---|
| 2,722,826 | 11/1955 | Milligan et al. | 73/64.45 |
| 2,782,628 | 2/1957 | Jacobs et al. | 73/64.45 |
| 2,847,852 | 8/1958 | Rhodes et al. | 73/64.45 |
| 4,220,120 | 9/1980 | Jackson et al. | 123/3 |
| 4,667,508 | 5/1987 | Soderstrom, III et al. | 73/64.45 |
| 4,783,989 | 11/1988 | Reed | 73/64.45 |
| 5,267,470 | 12/1993 | Cook | 73/118.1 |

FOREIGN PATENT DOCUMENTS 0779860  11/1980  U.S.S.R. .................... 73/64.45

*Primary Examiner*—Hezron E. Williams
*Assistant Examiner*—J. David Wiggins
*Attorney, Agent, or Firm*—Dennison, Meserole, Pollack & Scheiner

[57] ABSTRACT

A test procedure to determine the maximum safe altitude that an airplane can be operated at with a given batch of fuel. A pressure vessel is installed on an aircraft to receive a sample of the fuel to be tested. A pressure transducer mounted on the vessel measures the vapor pressure of the sample. The vapor pressure along with the outside air temperature, the carburetor temperature and the fuel temperature are compared with a set of criteria derived from a worse case airplane to yield the maximum safe altitude. The information may be derived manually or automatically by a process control computer.

15 Claims, 3 Drawing Sheets

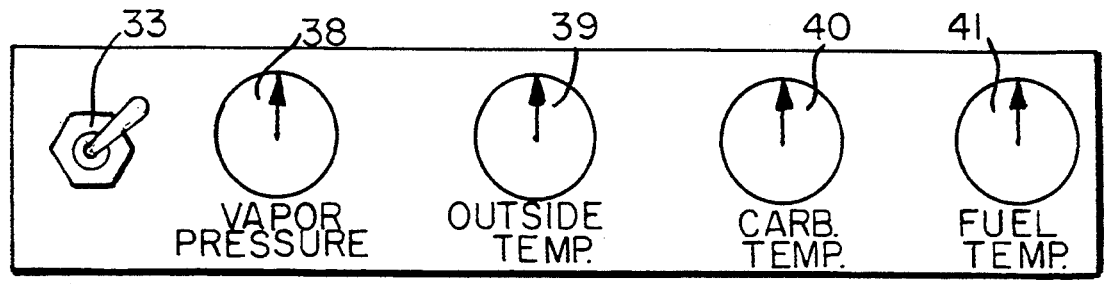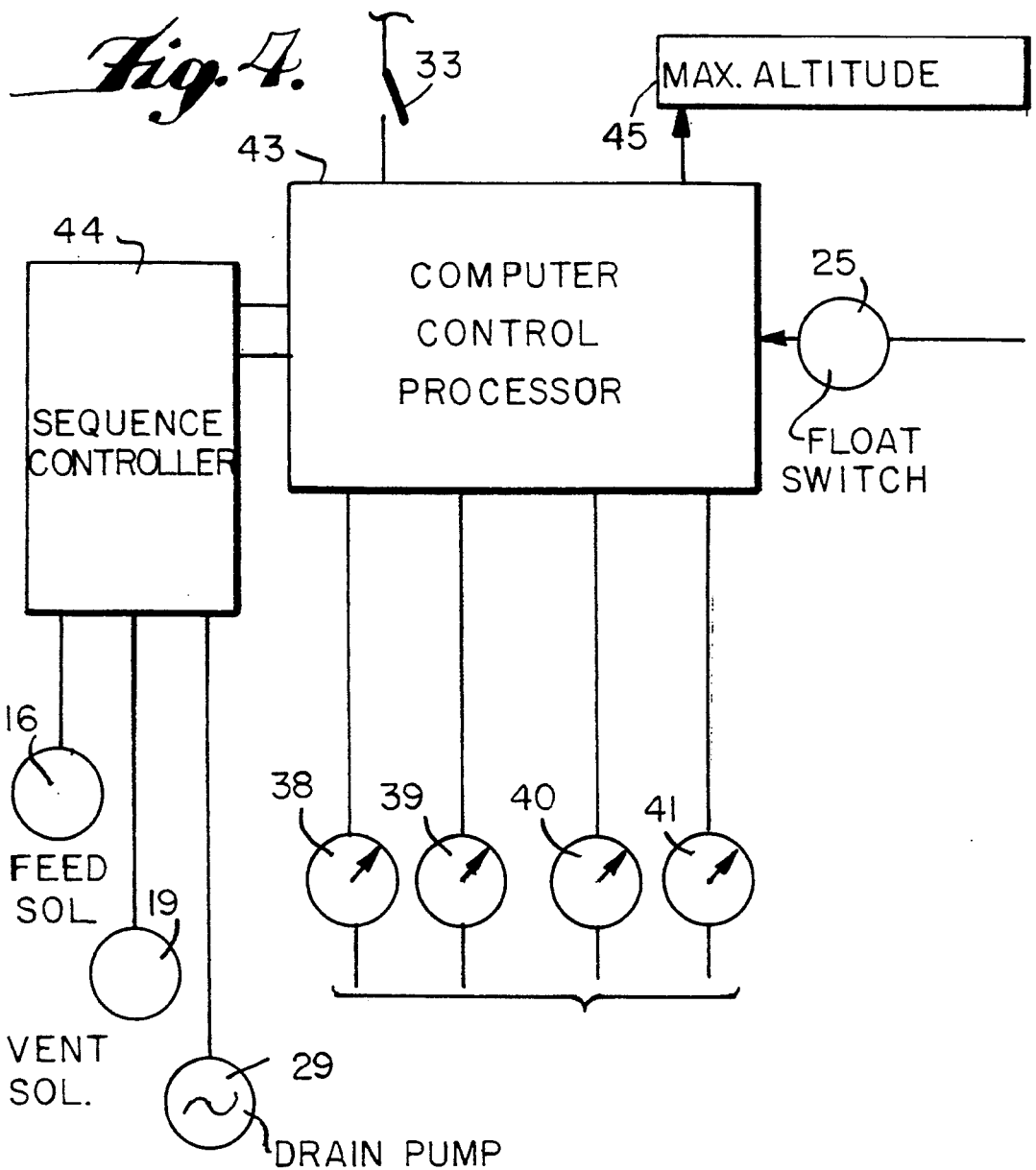

AIRCRAFT ANALYZER TO DETERMINE MAXIMUM SAFE ALTITUDE FOR A GIVEN BATCH OF FUEL

BACKGROUND OF THE INVENTION

This invention relates to a system and method to indicate to a pilot the maximum safe altitude to which he may fly an airplane with any given batch of fuel, regardless of the range of parameters of that fuel. The problem of fuel vapor lock in aircraft fuel systems and of pneumatic lock in aircraft carburetors is one that goes back to the early days of aviation. Gasoline is a volatile fluid which is subject, when used in airplanes, to conditions of rapid changes in pressure and temperature. As a result, vaporization and cavitation can take place in the lines and/or in the fuel pumps and fuel foaming or boiling (pneumatic lock) can take place in the carburetor. Either of these conditions can cause a loss in engine power with potentially catastrophic results.

These problems were originally dealt with by lowering the vapor pressure of the fuel to the lowest possible level while improving fuel system design. Typically, aviation gasoline has had a Reid vapor pressure (RVP) of 7 to 8 in an effort to offset the problem of vapor and pneumatic lock. Therefore, general aviation (G.A.) aircraft are certificated with this fuel, and must be recertificated if a fuel with a RVP higher than this is to be used.

In the early 1980's, as the availability of aviation fuel declined while its price increased, a gradual shift to the use of automotive fuel in aircraft took place. In addition, in more recent years the need to meet EPA requirements regarding the elimination of lead and other pollutants has forced refiners to experiment with new blends of aviation fuel. In order to provide some flexibility for the refiners, the maximum RVP of the new fuels was raised to 13.

It can be seen from the above that each airframe type originally certificated on aviation fuel with 7 to 8 RVP would have to go through a flight test program on 13 RVP fuel. Given the large number of airframes which would have to be recertificated, the test program approach would be costly and time consuming. A method of avoiding the need to evaluate each airframe would be a significant advance in the art.

SUMMARY OF THE INVENTION

The overall object of the present invention is to provide a system for evaluating, not the airframe, but the parameters of any batch of fuel following its introduction into an airplane's fuel tanks, and prior to takeoff. This invention will measure fuel vapor pressure, fuel temperature, and other fuel and atmosphere parameters, and report maximum allowable altitude to the pilot following engine start but prior to takeoff. By installing this invention and evaluating each batch of fuel, the pilot is informed to what altitude he may fly his airplane on any given day, considering those parameters that dictate whether a fuel will or will not give vapor related problems.

It is a further object of the invention to employ logic having a frame of reference based on flight testing a worse case airplane where the range of parameters which cause vapor and pneumatic lock are known.

It is another object of the invention to assemble the system from readily available components to reduce the cost of manufacture.

BRIEF DESCRIPTION OF THE DRAWINGS

FIG. 3 shows an instrument panel usable with the invention; and

FIG. 4 is a schematic diagram of an automated version of the FIG. 2 circuit.

DESCRIPTION OF THE PREFERRED EMBODIMENTS

Figure 1:
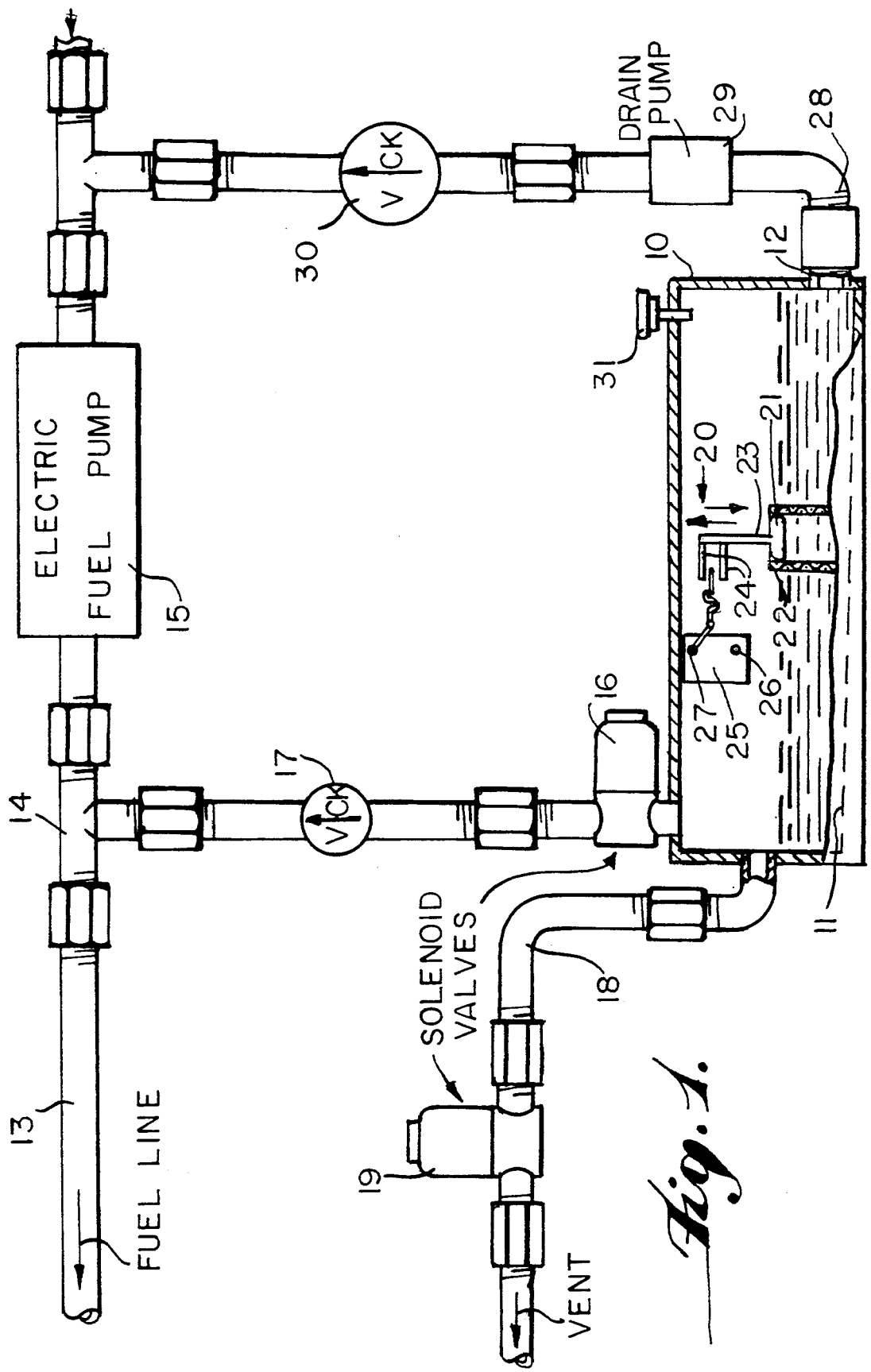
FIG. 1 is a schematic diagram of the mechanical components of the invention.

Referring now to the drawings and particularly to FIG. 1, the novel fuel-altitude-correlation system of this invention comprises a pressure vessel 10 for holding a predetermined amount of aviation fuel. The vessel is arranged to lie in a generally horizontal position with a bottom 11 slanted in the direction of a drain outlet 12. The pressure vessel is in fluid communication with the main engine fuel line 13 at a tee connection 14 on the pressure side of engine electric fuel pump 15. The flow of fuel from the main fuel line 13 to vessel 10 is controlled by a normally closed fuel control solenoid valve 16. A check valve 17 is installed between solenoid 16 and the connection 14 to prevent any backflow between the pressure vessel and the main fuel line 13.

A vent line 18 is connected to an upper portion of the pressure vessel to vent fuel vapor above the level of fuel in the pressure vessel. Opening and closing of the vent line is controlled by a normally closed venting solenoid 19.

A float switch 20 is mounted within the pressure vessel 10 to control solenoids 16 and 19 to permit vessel 10 to be charged with a predetermined amount of fuel and to subsequently permit an emptying of this fuel charge. Float switch 20 can comprise a float 21 retained in a guide 22 to rise and fall with the fuel level. A rod 23 connected to the float carries two switch operators 24 which engage an over center explosion proof switch 25. The float is shown in its vessel full position with switch 25 making contact with normally open terminal 27. As fuel leaves the vessel, the float falls until the upper switch operator 24 contacts over center switch 25, breaking contact 27 and making contact 26.

It should be understood that a wide variety of float switches and liquid level control circuits commonly used in the liquid level control arts may be employed here.

The pressure vessel is drained by means of a drain line 28 connecting drain outlet 12 with main engine fuel line 13 upstream of engine electric fuel pump 15. An electrically operated drain pump 29 is installed in the drain line to pump the fuel in vessel 10 back into the main fuel line at the completion of a test cycle. A check valve 30 on the discharge side of pump 29 prevents any backflow into vessel 10 when the drain pump 29 is idle.

A conventional pressure transducer 31 is mounted on the pressure vessel 10 to sense the vapor pressure of the fuel sample and to send a representative electrical signal to an indicating instrument on the instrument panel.

Figure 2:
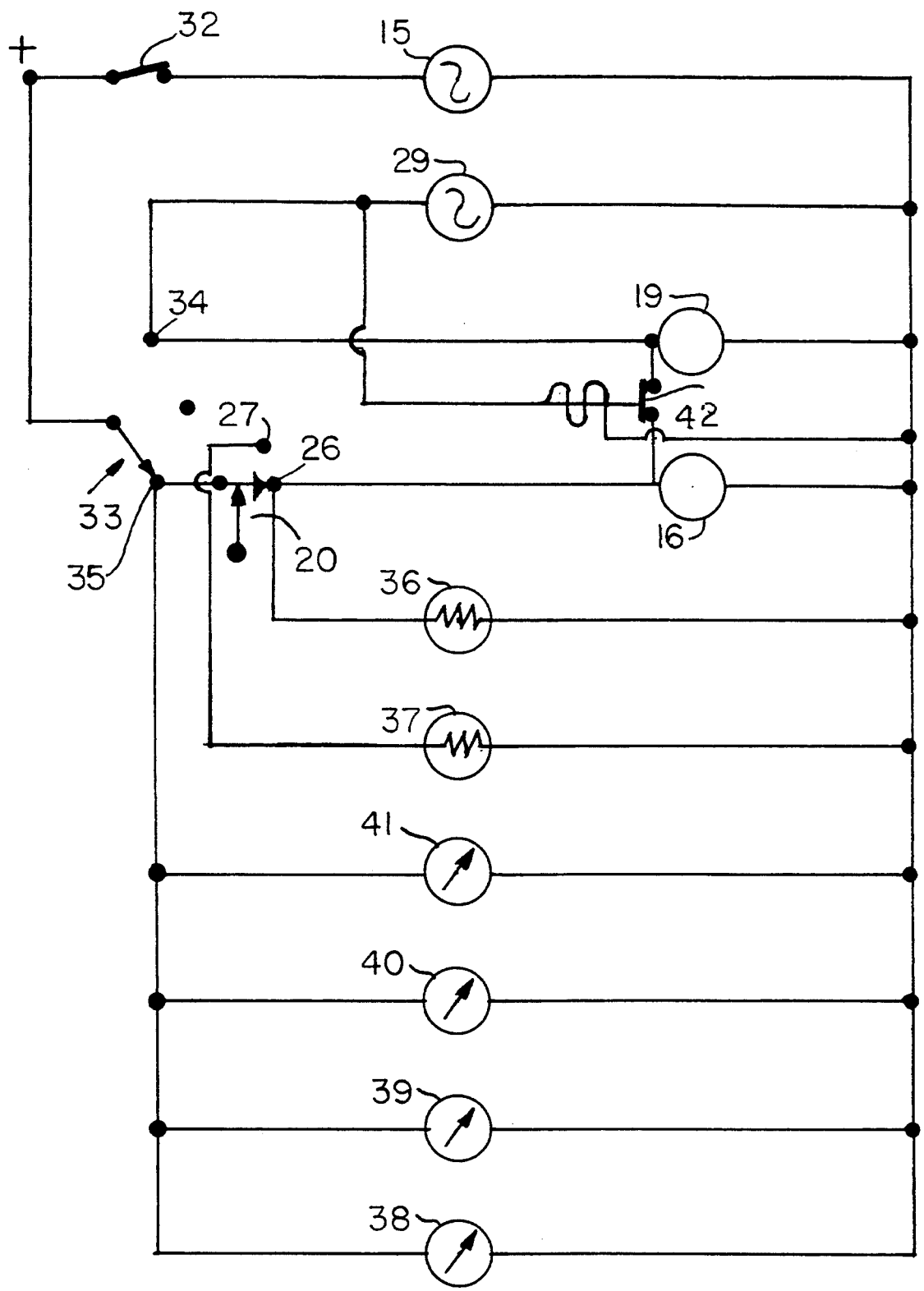
FIG. 2 is a schematic diagram of the electrical circuit for operating the FIG. 1 system manually.

The FIG. 1 assemblage comprises the mechanical components added to a typical aircraft to perform the fuel-altitude correlation test of the invention. These components are electrically connected in an overall test system as is explained in connection with the electrical schematic diagram of FIG. 2.

Ignition switch 32 is closed, energizing engine electric fuel pump 15. The aircraft engine is operated to clear any old fuel out of line 13 so fuel representative of the new batch is available for testing. A toggle switch 33 having a neutral position and two operating contact positions 34 and 35 is mounted on the instrument panel.

The test begins by depressing the toggle switch 33 to the contact position 35. Positive voltage passes through contact 35 to normally closed contact 26 of float switch 20. Contact 26 is closed since the pressure vessel 10 is empty at the beginning of the test and the float switch is in the bottom position. Feed solenoid valve 16 and venting solenoid 19 connected between contact 26 and ground are energized. Fuel under pressure from pump 15 flows through check valve 17 and solenoid valve 16 into vessel 10. Air and any vapor which may be present in vessel 10 is vented to the outside by means of vent line 18 and venting solenoid 19. An LED 36 connected between contact 26 and ground glows, signalling that the vessel is being charged with fuel.

When the fuel in vessel 10 reaches a level as determined by float switch 20, the lower switch operator 24 operates switch 25 to the contact position 27 shown in FIG. 1 closing solenoid valves 16 and 19. An LED 37 connected between contact 27 and ground glows, signalling a charged vessel.

While toggle switch 33 is in the contact. 35 position, a number of sensors are activated which have readouts on the instrument panel as shown in FIG. 3. Vapor pressure meter 38 reads the pressure sensed by pressure transducer 31. An outside air temperature meter 39 senses the temperature of outside air. A carburetor temperature meter 40 senses the temperature of the carburetor. A fuel temperature meter 41 senses the fuel temperature at the carburetor. The temperature meters may employ a thermistor as the actual temperature sensing element.

After the pressure vessel has been charged with fuel and solenoids 16 and 19 deenergized, a period of about ten minutes should elapse before a test reading is taken. During this time the pilot continues with his checklist and proceeds to the runway.

After about ten minutes has elapsed, the pilot takes down the readings of meters 38, 39, 40 and 41 and plots them on a specially drawn chart which uses a predetermined set of criteria obtained from a worse case aircraft. The data so plotted on the graph will show the maximum safe altitude the airplane can be flown for the fuel present in the tanks at that fuel and carburetor temperature.

With a little experience, the pilot can mentally estimate the maximum safe altitude from the readings on meters 38, 39, 40 and 41. Also, a hand held or panel mounted calculator can be programmed to read the maximum safe altitude after keying in the data from meters 38–41.

After a maximum safe altitude reading is obtained, the system is reset to a standby condition. Toggle switch 33 is moved from contact position 35 to contact position 34. Vent solenoid 19 is energized to open the vent line. At the same moment, relay switch 42 is energized, opening the circuit to feed solenoid 16, keeping the fuel feed line to vessel 10 closed. Drain pump 29 is energized and pumps the fuel out of vessel 10 back into the main supply. After a predetermined interval of time, the pressure vessel 10 is emptied of fuel, and the float switch drops to contact position 26. Toggle switch 33 is then moved to its neutral position to terminate the cycle.

Referring now to FIG. 4, a schematic circuit is disclosed for automatically performing the manual functions described above in connection with FIG. 2. A computer control processor 43 is arranged to receive input data from vapor pressure meter 38, outside air temperature meter 39, carburetor temperature meter 40, fuel temperature meter 41 and float switch 25. The computer 43 controls a sequence controller 44 which operates feed solenoid 16, venting solenoid 19 and drain pump 29 in proper sequence. The logic derived by flight testing a worse case airplane is programmed into the computer 43.

In operation, a test cycle commences by momentarily depressing switch 33. The computer control processor 43 reads the level of float switch 25. If the float is down, the computer signals the sequence controller to open feed solenoid 16 and vent solenoid 19 allowing fuel to flow from the engine fuel line into vessel 10. When the float indicates to the computer that a proper sample of fuel has been obtained, solenoids 16 and 19 are closed. A time delay of about 10 minutes is programmed into the computer after which the vapor pressure 38, along with the outside air temperature 39, the carburetor temperature 40 and the fuel temperature 41 are processed by the computer using the predetermined logic, previously obtained, to provide a maximum safe altitude at digital display 45.

After delivering a reading, the computer then opens vent solenoid 19 and activates drain pump 29. When the float 25 drops, indicating the pressure vessel is empty, the vent solenoid 19 is closed and the drain pump shut off. Thus the pressure vessel is empty and the test system is ready for the next fuel sample to be drawn later in the flight, or prior to the next flight. As the flight progresses the fuel and carburetor temperatures may decrease, and another test could be done in flight. Given that this occurs, a higher altitude may be allowed.

Although the invention has been described with reference to a specific embodiment and method of making, many variations will be apparent to those skilled in the art, without departing from the scope of the invention as described in the following claims.

I claim:

1. An aviation fuel test system for an aircraft having an electric fuel pump for drawing fuel from a fuel supply intake and delivering it under pressure to an aircraft engine, said test system comprising: a pressure vessel to contain a predetermined sample of fuel, conduit means for connecting said pressure vessel to the pressure side of said electric fuel pump, a first solenoid valve mounted in said conduit means, a vent pipe connected to said pressure vessel, a second solenoid valve mounted in said vent pipe, liquid level control means for sensing the fuel level in said pressure vessel, said liquid level control means electrically controlling said first and second solenoids, a drain line connecting said pressure vessel to said fuel supply intake, and an electric drain pump mounted in said drain line.

2. The combination of claim 1 including system switching means for supplying power to the electrical components of said test system in accordance with a predetermined sequential program.

3. The combination of claim 2 wherein said liquid level control means comprises a float switch having a first and second switching position, said first switching position representing an empty pressure vessel and said second switching position representing a predetermined full pressure vessel position when said float switch is energized by said system switching means.

4. The combination of claim 3 wherein said first and second solenoids are energized when said float switch is in said first switching position to permit entry of fuel into said pressure vessel and said first and second solenoids are deenergized when said float switch is in said second switching position.

5. The combination of claim 4 including signalling means responsive to said first and second float switching positions to indicate whether the pressure vessel is full or empty.

6. The combination of claim 4 including a pressure transducer mounted on said pressure vessel to sense the vapor pressure of the fuel in said pressure vessel.

7. The combination of claim 6 including circuit means activated when said system switching means energizes said float switch to transmit a signal representative of vapor pressure in said pressure vessel to the aircraft instrument panel.

8. The combination of claim 7 wherein said circuit means includes temperature sensing means for measuring the outside air temperature, the carburetor temperature and the fuel temperature and sending a representative signal to the instrument panel.

9. The combination of claim 8 including vapor pressure, outside air temperature, carburetor temperature and fuel temperature indicators mounted on said instrument panel to receive said representative signals whose readings are then compared with a previously determined frame of reference to give an indication of the maximum safe operational altitude.

10. The combination of claim 9 wherein upon completion of the test cycle yielding a maximum safe altitude, the system switching means deenergizes said float switch and energizes said drain pump, said second solenoid valve and a relay switch to maintain said first solenoid valve in a closed position whereby said pressure vessel is drained of its fuel.

11. A method for determining the maximum safe operating altitude of an airplane with a given batch of fuel comprising the steps of: providing a pressure vessel in fluid communication with the fuel supply of the airplane, supplying said pressure vessel with a predetermined fuel sample from said fuel supply, measuring the vapor pressure of the fuel sample in the pressure vessel, measuring the outside air temperature, the carburetor temperature and the fuel temperature, feeding the vapor pressure, outside air temperature, carburetor temperature and fuel temperature measurements to a computer controlled processor, comparing the measurements with a predetermined set of criteria stored in the computer to yield a readout indicating the maximum safe altitude.

12. The method of claim 11 further comprising the step of providing a time delay of about ten minutes between the steps of supplying the pressure vessel with fuel and feeding the vapor pressure and temperature measurements to the computer.

13. The method of claim 11 further comprising the step of draining the pressure vessel of fuel and returning it to the fuel supply after the maximum readout is given.

14. The method of claim 11 wherein the predetermined set of criteria stored in the computer is derived from flight testing the fuel supply in a worse case airplane.

15. The method of claim 12 wherein the computer control processor is programmed to perform the steps of supplying the pressure vessel with fuel and taking the vapor pressure and temperature measurements after the time delay.

* * * * *